United States Patent [19]

Schuss et al.

[11] 4,321,039

[45] Mar. 23, 1982

[54] DENTAL HANDPIECE

[75] Inventors: Werner Schuss, Heppenheim; Hans J. Klose, Hemsbach, both of Fed. Rep. of Germany

[73] Assignee: Siemens Aktiengesellschaft, Berlin & Munich, Fed. Rep. of Germany

[21] Appl. No.: 167,060

[22] Filed: Jul. 9, 1980

[30] Foreign Application Priority Data

Jul. 20, 1979 [DE] Fed. Rep. of Germany ....... 2929483

[51] Int. Cl.³ .............................................. A61C 1/12
[52] U.S. Cl. ...................................... 433/82; 433/126
[58] Field of Search ...................... 433/82, 84, 85, 126

[56] References Cited

U.S. PATENT DOCUMENTS

| 3,894,338 | 7/1975 | Loge et al. | 433/82 |
| 3,936,940 | 2/1976 | Loge | 433/82 |
| 4,184,256 | 1/1980 | Loge et al. | 433/82 |
| 4,212,640 | 7/1980 | Loge et al. | 433/82 |
| 4,217,101 | 8/1980 | Loge | 433/82 |

Primary Examiner—Gene Mancene
Assistant Examiner—John J. Wilson
Attorney, Agent, or Firm—Hill, Van Santen, Steadman, Chiara & Simpson

[57] ABSTRACT

A dental handpiece comprising a drive section with a drive shaft for driving a tool receiving socket mounted for rotation in an end of a handle section which handle section is coupled for relative rotation on the drive section, said dental handpiece having at least one cooling medium line being formed by a line segment arranged in each of said sections for conveying the medium to a nozzle adjacent the socket, and a rotatable coupling for the cooling medium lines characterized by the rotatable coupling being formed by a first and second sleeves being telescopically assembled together for relative rotation, one of said sleeves having an annular groove for each of the cooling medium lines and the other of the two sleeves having a radial opening in communication with each of the annular channels, said sleeves being detachably connected to the respective section to rotate therewith.

8 Claims, 3 Drawing Figures

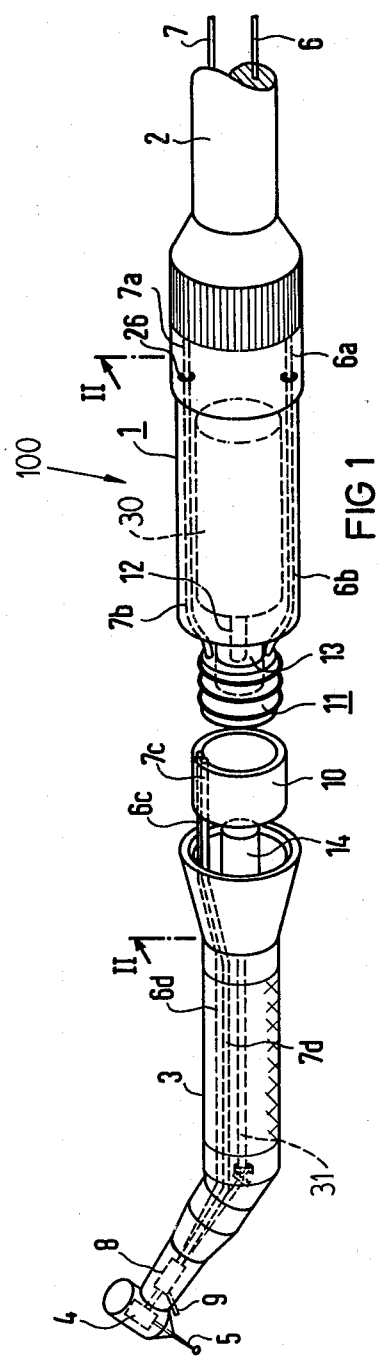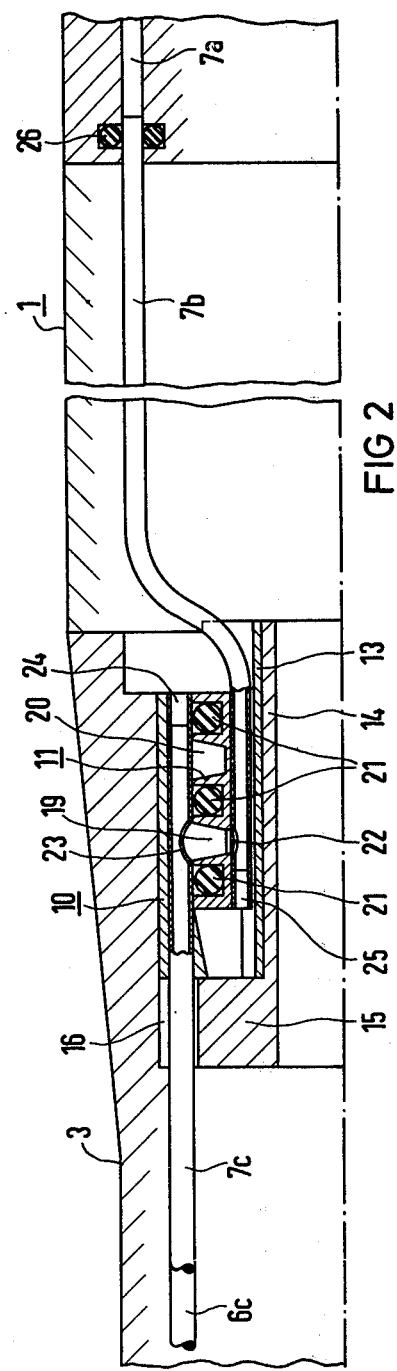
FIG 1
FIG 2

DENTAL HANDPIECE

BACKGROUND OF THE INVENTION

The present invention is directed to a dental handpiece comprising a drive section or part, which has a drive shaft extending from a drive motor, a handle section, which is mounted for rotation on the drive section and contains a drive train for transferring rotation of the drive shaft to a rotatable acceptance socket for receiving a tooth treatment instrument such as a drill. The dental handpiece has cooling medium lines comprising line segments incorporated in each of the drive and the handle sections which line segments are interconnected by a coupling formed by a ring channel in one of the handpiece sections and a radial opening communicating the ring channel being provided in the other of the handpiece sections.

Dental handpieces, in which a cooling line is guided in the various handpiece sections, are recently enjoying an ever increasing use and such a handpiece is described for example in U.S. Pat. No. 4,007,529, which was based on German O.S. No. 24 31 472. In such a handpiece, problems have occurred with being able to readily clean or exchange the cooling lines which have a relatively small cross section and therefore are easily clogged.

In German O.S. No. 2,653,588, an attempt to solve this problem for the handle-side handpiece section was suggested. Such a solution is that an externally accessible closing or sealing member is provided on the outer jacket of the handle section. The closing or sealing member covers the location at which a transition is provided from a rectilinear, axial parallel proceeding segment or section of the cooling line to the radial section which extends to the ring channel. This closing or sealing member can be removed in case of a possible clogging of the segment. In the case of such a construction, several disadvantages occur. For example, in addition to O-ring seals on the sealing member, which are necessary for the rotation of the two handpiece sections, additional sealing locations are created. Moreover, the proposed solution does not solve the problem of providing easy cleaning and/or exchanging of possibly clogged lines or conduits directly at the rotary coupling location. For example, in the region of the transfer of the agent from the drive section to the handle section and specifically in the region of the drive section itself, the solution does not provide an easy cleaning and/or exchanging of clogged lines.

SUMMARY OF THE INVENTION

The present invention is directed to an improved dental handpiece of a structure in which the continued conveyance of a cooling medium from the drive section to the handle section can be obtained without additional sealing locations and with a low risk of contaminating or clogging of the line segments. In addition, the construction provides a possibility of easy cleaning and/or easy exchange of structurally simple parts in case of a possible clogging.

To accomplish these goals, the present invention is directed to an improvement in a dental handpiece having a drive section detachably connected to a handle section for relative rotation therewith, the drive section having a drive motor with a drive shaft, the handle section having means for transferring the rotation of the drive shaft to a rotatable acceptance socket for receiving a tool treatment instrument, the handpiece having at least one cooling medium line being formed by line segments arranged in the drive and handle sections for conveying a cooling medium to a nozzle adjacent the acceptance socket, each of said cooling medium lines including a rotatable coupling of an annular channel and a coacting radial opening to enable relative rotation between a line segment in the drive section and a line segment in the handle section. The improvement comprises the rotational coupling being formed by first and second sleeves being telescopically received together for relative rotation therebetween, one of the first and second sleeves having an annular groove for each of the cooling medium lines, the other of the first and second sleeves having a radial opening in communication with each of the annular channels, the first sleeve having a cooling line segment for each cooling medium and being detachably mounted on the drive section by means preventing relative rotation between the first sleeve and the drive section, and the second sleeve having a cooling line segment for each cooling medium line and being detachably mounted on the handle section by means for preventing relative rotation between the handle section and the second sleeve so that each of the sleeves rotates with the respective section as a result of the rotation between the sections.

A significant advantage of the improvement is that the cooling mediums or coolants are not guided or conveyed in or through the respective guide sleeves surrounding the drive shaft. On the contrary, for the purpose of support-mounting and guiding of the coolant lines, separate sleeves are provided which are simple and inexpensive to manufacture from an engineering standpoint. In addition, only the O-ring seals at the medium transfer location from the one to the other handpiece sections, which O-ring seals are necessary in any case on account of the rotatability of the two handpiece sections, are required and no additional sealing locations are necessary.

BRIEF DESCRIPTION OF THE DRAWINGS

FIG. 1 is a perspective view of a dental handpiece in accordance with the present invention in a partially disassembled state;

FIG. 2 is a partial longitudinal cross-sectional view taken in the area of lines II—II of FIG. 1 with the handpiece sections in the assembled state.

DESCRIPTION OF THE PREFERRED EMBODIMENTS

Figure 3:
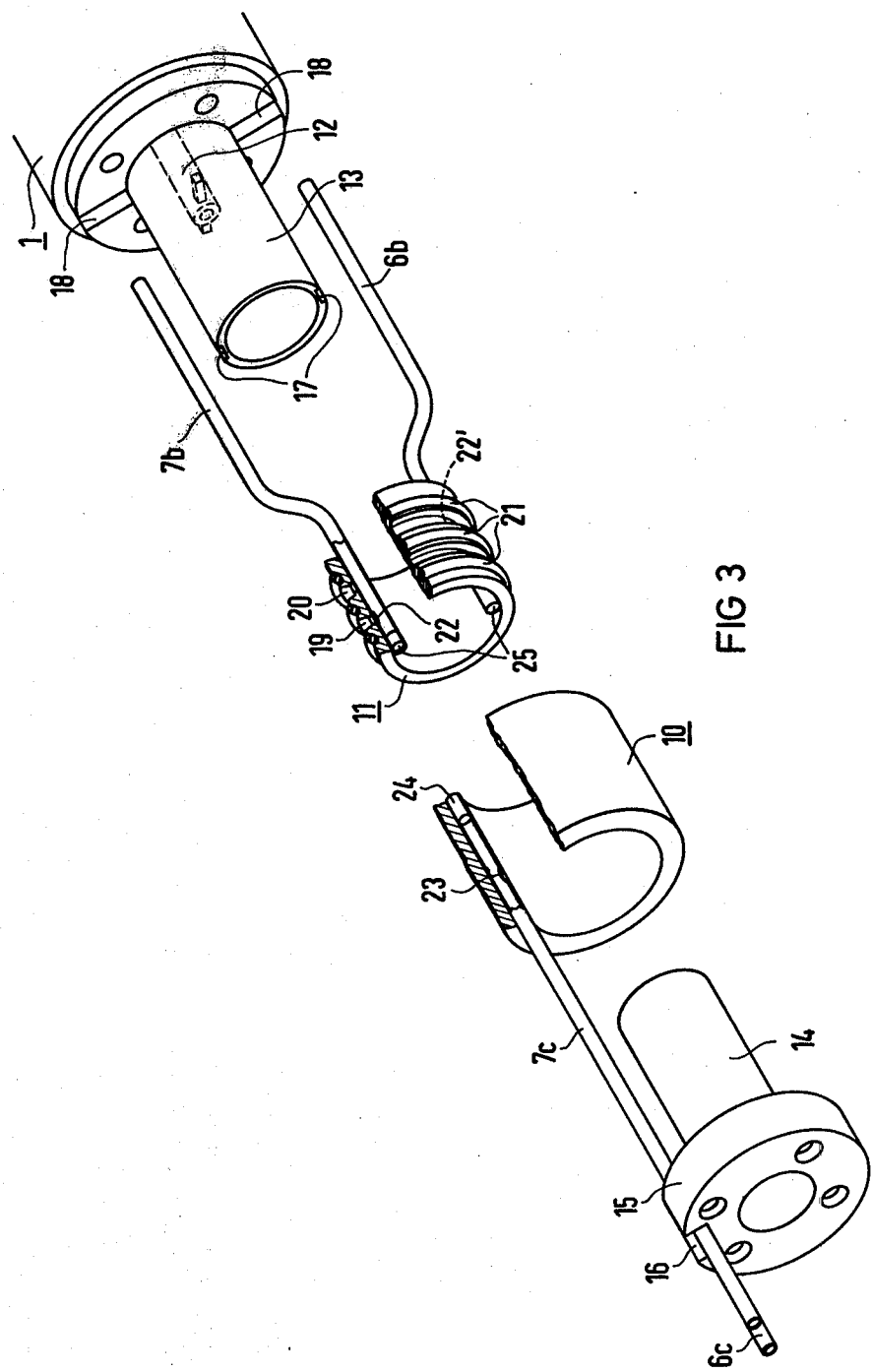
FIG. 3 is an exploded isometric view with portions in cross-section for purposes of illustration of the improvement of the present invention.

The principles of the present invention are particularly useful in a dental handpiece generally indicated at 100 in FIG. 1. The dental handpiece includes a plurality of handpiece sections such as a drive section 1 and a handle section 3 which are coupled together for relative movement by a coupling which includes a conventional detachable connection which is not illustrated. At an end opposite the connection to the handle section 3, the drive section 1 is connected to a supply hose 2. The handle section 3 is a so called angled handpiece and has a head section, which contains an acceptance socket 4 for receiving a tool or a tooth treatment instrument such as a drill 5. The socket 4 is mounted for rotation in the head of the handle piece 3 and is driven by a motor 30 in the drive section 1. The motor 30 has a drive shaft 12 connected in a known manner by a plurality of drive shafts 31 in the handle section 3 to the socket 4. The motor 30 may be either an electrical motor or an air motor and receives its drive energy through an appropriate conduit or conductor in the supply hose 2.

In order to cool the drill or treatment instrument 5, or to cool the area on which the drill is acting on, a pair of cooling medium lines or conduits 6 and 7 are provided in the supply hose and are in communication with separate line segments 6a–6d and 7a–7d. The lines segments 6d and 7d merge in a mixing chamber 8, which has an outlet in the form of a nozzle 9 which will direct a mixture of the cooling agents or media in the vicinity of the treatment tool 5.

In order to form a rotatable coupling at the connection of the handle section 3 on the drive section 1, coupling means are provided that include a pair of sleeve members 10 and 11. The first sleeve member 11, as illustrated, is telescopically received in the second sleeve member 10 and, as illustrated in FIG. 2, has means to enable forming the rotatable coupling between the segments such as line segments 7b and the line segments 7c.

As illustrated, the drive section 1 has a first guide sleeve 13 which projects from the housing of the section 1 and telescopically receives the first sleeve 11. In a similar manner, the housing of the handle section 3 receives a second guide member or sleeve 14 which has a flange 15 at the base. When the two sections 1 and 3 are joined together, the guide sleeve 14 is telescopically received in the guide sleeve 13.

As best illustrated in FIG. 3, the sleeve 10 is connected to a line segment 6c and a line segment 7c which extend into bores or grooves formed in the sleeve. In a similar manner, two cooling line segments 6b and 7b are received on the inner cylindrical surface of the sleeve 11 and as illustrated are diametrically opposed to each other. The first guide sleeve 13 has a pair of diametrically opposed longitudinally extending grooves 17 which merge or intersect with grooves 18 in the housing of the drive section 1. Thus, when the sleeve 11 is telescopically received on the guide sleeve 13, the two line segments 6b and 7b are received in the grooves 17 as well as the grooves 18 and prevent relative rotation between the sleeve 11 and the guide sleeve 13. It is noted that the free ends of the segments 6b and 7b are received in passages 6a and 7a respectively and sealed there by "O" rings 26. As mentioned hereinabove, the two line segments 6c and 7c, which are connected to the sleeve 10, extend parallel to each other and the flange 15 of the second guide sleeve 14 has a groove 16 for receiving these segments 6c and 7c so that the segments 6c and 7c coact with the grooves 16 to form means to prevent relative movement between the sleeve 10 and the guide sleeve 14.

As illustrated in FIGS. 2 and 3, the sleeve 11 contains two ring grooves 19 and 20, which are sealed from one another by means of three O-rings 21. For purposes of transferring fluid from the line segments 7b, it has a bore 22 which is in communication with the groove 19. In a similar manner, the line segment 6b has a bore 22' as indicated in FIG. 3 which is communication with the groove 20. Each of the line segments 6c and 7c has a radial opening such as the radial opening 23 in the line segment 7c which will be aligned with the corresponding annular grooves such as 19 when the sleeve 10 is telescopically received on the sleeve 11 (see FIG. 2).

Thus, fluid in segment 7b passes through opening 22 into the groove 19. From the groove 19, fluid passes through the opening 23 and into the segment 7c.

The ends of each of the sleeves such as 6c and 7c are closed by detachable or removable sealing plugs 24 while the ends of the segments 6b and 7b are closed by removable plugs 25. Instead of utilizing a removable plug for sealing the ends, it is possible that the tubes forming the segments such as 7b and 7c are received in blind or dead end bores in the respective sleeve. As illustrated in FIG. 2, the other end of each of the line segments 6b and 7b are received in the associated channel 6a and 7a with the channel having a sealing O-ring such as 26. While not illustrated, the opposite end of each of the segments 6c and 7c are connected by appropriate seals to the segments 6d and 7d.

When initially removing the handle section 3 from the drive section 1, the sleeves 10 and 11 will initially remain on the respective handpiece sections. This is due to the consequence of the presence of friction locking and/or a positive closure or locking mechanism between the sleeve 11 and the guide sleeve 13 as well as the line segments 7b and the O-ring seal 26. In a similar manner, the line segments 6c and 7c in the groove 16 and the non-illustrated O-ring seals corresponding to O-ring seals 26 will keep the sleeve 10 on the drive section 3. If the drive section 1 and the handle section 3 are separated from one another, the possibility exists of slipping the sleeve 11, which acts as a carrier for the ends of the segments 6b and 7b, off of the drive section 1, which is possibly due to the O-ring plug type connection of the line sections 7a and 7b wherein the section 7a is expediently a bore in which the line segment 7b is inserted. Likewise, the sleeve 10 with the two line segments 6c and 7c can also be slipped off of the handle section 3 for cleaning and replacement purposes. Since the two sleeves 10 and 11 are arranged concentrically relative to one another and the parts of the sleeve with the segments are simple to manufacture from an engineering standpoint, a possible replacement of the line segments such as 6c and 7c as well as 6b and 7b can be carried out in a cost and time saving fashion.

It is also conceivable that within the scope of the invention to design the two sleeves 10 and 11 as a constructural or coupling unit, which although axially separable from one another is not operatively separable without the aid of a special tool. The constructional unit could be so connected with a drive section, that upon removal of the handle section from the drive section, the constructural unit would remain on the drive section. In the case of the replacement of the handle part or section, for example, in order to replace an angled handpiece handle part with a straight handpiece section, the rotary coupling or connection would remain on the drive section.

Although various minor modifications may be suggested by those versed in the art, it should be understood that we wish to embody within the scope of the patent granted hereon, all such modifications as reasonably and properly come within the scope of our contribution to the art.

We claim:

1. In a dental handpiece having a drive section detachably connected to a handle section for relative rotation therewith, said drive section having a housing containing a drive motor with a drive shaft and having an axially extending guide sleeve projecting from an end thereof, and said handle section having means for transferring the rotation of the drive shaft to a rotatable acceptance socket for receiving a tooth treatment instrument, said handpiece having at least one cooling medium line being formed by line segments arranged in said drive section and said handle section for conveying a cooling medium to a nozzle adjacent said acceptance socket, each of said cooling medium lines including a rotatable coupling of an annlar channel and a coacting radial opening to enable relative rotation between a line segment in the drive section and a line segment in the handle section, the improvements comprising the handle section having a guide sleeve projecting from an end thereof and being telescopically received in the guide sleeve of the drive section, the rotatable couplings being formed by first and second sleeves being telescopically received together for relative rotation therebetween, one of said first and second sleeves having an annular groove to form the annular channel for each of the cooling medium lines, the other of said first and second sleeves having a radial opening in communication with each of the annular channels, said first sleeve having a cooling line segment for each cooling medium line and being detachably and telescopically mounted on the guide sleeve of the drive section by means for preventing relative rotation between the first sleeve and the drive section, said means for preventing relative rotation including an axially extending groove in said guide sleeve of the drive section and a groove in the housing of the drive section for receiving each line segment secured to the first sleeve, and said second sleeve having a cooling line segment for each cooling medium line and being detachably mounted on the handle section by means for preventing relative rotation between the handle section and the second seleve so that each of the sleeves rotate with their respective section as a result of the rotation between the sections.

2. In a dental handpiece according to claim 1, wherein the first and second sleeves are telescopically interconnected by a separable axial connection.

3. In a dental handpiece according to claim 2, wherein the separable axial connection is provided by means of a frictional locking between the first and second sleeves and a positive closure therebetween.

4. In a dental handpiece according to claim 1, wherein the guide sleeve of the handle section has an annular flange adjacent the handle portion, and the means for preventing the relative rotation between the second sleeve and the handle section including grooves in the annular flange of the guide sleeve of the handle section for receiving the line segments secured to the second sleeve.

5. In a dental handpiece according to claim 4, wherein each of the coolant line segments is secured to its respective sleeve and has an end adjacent said sleeve closed by a removable plug.

6. In a dental handpiece having a drive section detachably connected to a handle section for relative rotation therewith, said drive section having a projecting guide sleeve and a drive motor with a drive shaft, and said handle section having means for transferring the rotation of the drive shaft to a rotatable acceptance socket for receiving a tooth treatment instrument, said handpiece having at least one cooling medium line being formed by line segments arranged in said drive section and said handle section for conveying a cooling medium to a nozzle adjacent said acceptance socket, each of said cooling medium lines including a rotatable coupling of an annular channel and a coacting radial opening to enable relative rotation between a line segment in the drive section and a line segment in the handle section, the improvement comprising the rotatable couplings being formed by a first and second sleeve being telescopically received together for relative rotation therebetween and having a separable axial connection being formed by means for a frictional locking between the first and second sleeves and a positive closure therebetween, one of said first and second sleeves having an annular groove forming the annular channel for each of the cooling medium lines, the other of said first and second sleeves having a radial opening in communication with each of the annular channels, said first sleeve being telescopically received on the guide sleeve and having a cooling line segment for each cooling medium line and being detachably mounted on the drive section by means preventing relative rotation between the first sleeve and the drive section, said second sleeve having a cooling line segment for each cooling medium line and being detachably mounted on the handle section by means for preventing relative rotation between the handle section and the second sleeve, and the handle section having a guide sleeve with a flange telescopically receiving the guide sleeve of the drive section and being coaxial with the first and second sleeves, said means for preventing relative rotation between the first sleeve and the drive section including the guide sleeve of the drive section having longitudinal extending grooves for receiving portions of the line segments and the drive section having grooves for receiving said line segments, and said means for preventing relative rotation between the second sleeve and the handle section including the flange of the guide sleeve of the handle section having grooves receiving said line segments attached to the second sleeve so that each of the sleeves rotates with their respective section as a result of the rotation between the section.

7. In a dental handpiece according to claim 6, wherein each of the cooling line segments on a free end adjacent the respective sleeve is closed by a removable plug.

8. In a dental handpiece having a drive section detachably connected to a handle section for relative rotation therewith, said drive section having a projecting guide sleeve and a drive motor with a drive shaft, and said handle section having means for transferring the rotation of the drive shaft to a rotatable acceptance socket for receiving a tooth treatment instrument, said handpiece having at least one cooling medium line being formed by line segments arranged in said drive section and said handle section for conveying a cooling medium to a nozzle adjacent said acceptance socket, each of said cooling medium lines including a rotatable coupling of an annular channel and a coacting radial opening to enable relative rotation between a line segment in the drive section and a line segment in the handle section, the improvement comprising the rotatable couplings being formed by first and second sleeves being telescopically received together for relative rotation therebetween and having a separable axial connection being formed by means for a frictional locking between the first and second sleeves and a positive closure therebetween, one of said first and second sleeves having an annular groove to form the annular channel for each of the cooling medium lines, the other of said first and second sleeves having a radial opening in communication with each of the annular channels, said first sleeve being telescopically received on the guide sleeve and having a cooling line segment for each cooling medium line and being detachably mounted on the drive section by means for preventing relative rotation between the first sleeve and the drive section, said second sleeve having a cooling line segment for each cooling medium line and being detachably mounted on the handle section by means for preventing relative rotation between the handle section and the second sleeve, and the handle section having a guide sleeve telescopically receiving the guide sleeve of the drive section and being coaxial with the first and second sleeves, said means for preventing relative rotation between the first sleeve and the drive section including the guide sleeve of the drive section having longitudinal extending grooves for receiving portions of the line segments and the drive section having grooves for receiving said line segments, and said means for preventing relative rotation between the second sleeve and the handle section including the handle section having grooves receiving said line segments attached to the second sleeve so that each of the sleeves rotates with their respective section as a result of the rotation between the sections.

* * * * *